(12) United States Patent
Kasaoka et al.

(10) Patent No.: US 6,228,637 B1
(45) Date of Patent: May 8, 2001

(54) RECOMBINANT VECTOR, METHOD FOR GIVING IMMUNITY AGAINST PVY-T TO POTATO PLANT, AND POTATO PLANT HAVING IMMUNITY AGAINST PVY-T

(75) Inventors: Keisuke Kasaoka, Shizuoka; Naoto Kadotani, Tokyo; Shigeru Kuwata; Yumiko Hayashi, both of Yokohama, all of (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

(21) Appl. No.: 08/558,935

(22) Filed: Nov. 13, 1995

Related U.S. Application Data

(63) Continuation of application No. 08/139,157, filed on Oct. 21, 1993, now abandoned.

(30) Foreign Application Priority Data

Oct. 21, 1992 (JP) .................................... 4-308278

(51) Int. Cl.⁷ .................................................. C12N 15/00
(52) U.S. Cl. ........................................................ 435/320.1
(58) Field of Search ........................... 800/205, DIG. 42; 435/178.3, 240.51, 320.1

(56) References Cited

U.S. PATENT DOCUMENTS 4,970,168 * 11/1990 Tumer ................................ 435/317.1

FOREIGN PATENT DOCUMENTS

| | | |
|---|---|---|
| 806481 | * 11/1997 | (EP) . |
| WO8905858 | 6/1989 | (WO) . |
| WO8912100 | 12/1989 | (WO) . |
| WO9002184 | 3/1990 | (WO) . |

OTHER PUBLICATIONS

Barker et al (1984) Ann Appl. Biol 105 (3):539–546.*
Hidaka et al (1985) J. Biochem 97:161–171.*
Hay et al (1989) Arch virol 107:111–122.*
Nejidat et al (1990) Physiol. Plant. 80:662–668.*
Farinelli et al Bio/Technology vol. 10 1020–1025, Sep. 1992.*
Clark et al. "engineering virus resistance in transgenic plants". Plant Biol. vol. 11, pp 273–283, 1990.*
Cuozzo et al. "Virual protection in transgenic tobacco plants expressing the cucumber mosaic virus coat protein or its antisense RNA". Bio/Technology. vol. 5, No. 6, pp 549–554, 557, 1988.*
Kawchuk et al. "Sense and antisense RNA–mediated resistance to potato leafroll virus in Russet Burbank potato plants". Mol. Plant–Microbe Interact. vol. 4, No. 3, pp 247–253, 1991.*
Hull et al. "Approaches to nonconventional control of plant virus diseases". Crit. Rev. Plant. Sci 11. vol. 1, pp 17–33, 1992.*
N.Shigetou (1992) *Plant Cell Technology* 4 (2):101–109.
A. Inoue (1991) *Ann. Phytopath. Soc. Japan* 57:615–622.
N. Nitta et al. (1988) *Ann. Phytopath. Soc. Japan* 54:516–522.
G. An et al. (1988) *Plant Molecular Biology Manual* A3:1–19.
Udagawa et al. (1972) *Japan Plant Pathology Assoc. Report* 38 (3):210, Ab. 150.
P. S. Thomas (1980) *Proc. Natl. Acad. Sci. USA* 77 (9):5201–5205.
R. Van der Vlugt et al. (1989) *J. Gen. Virol.* 70:229–233.
C. Lawson et al. (1990) *Bio/Technology* 8:127–134.
L. Farinelli et al. (1992) *Bio/Technology* 10:1020–1025.
S. Hidaka et al. (1985) *J. Biochem.* 97:161–171.

* cited by examiner

*Primary Examiner*—Anthony C. Caputa
*Assistant Examiner*—Brenda G. Brumback
(74) *Attorney, Agent, or Firm*—Birch, Stewart, Kolasch & Birch, LLP

(57) ABSTRACT

A recombinant vector which can transform potato plants so as to confer upon the potato plant immunity against potato virus Y necrosis line is disclosed. The recombinant vector according to the present invention comprises a promoter which functions in a potato plant cell; an operably linked leader sequence of RNA4 of cucumber mosaic virus, which is located downstream of the promoter; and an operably linked sequence which encodes a coat protein of potato virus Y necrosis line, which is located downstream of said leader sequence; and the recombinant vector is capable of transforming potato plants.

8 Claims, 4 Drawing Sheets

GNDTIDAGGSTKKDVKQEQGSIQPNLNKEKEKDLNVGTSGTHTVPRIKAITSKMRMPKSKGATVLNLEHLL
EYAPQQIDISNTRATQSQFDTWYEAVQLAYNIGETEMPTVMNGLMVWCIENGTSPNINGVWVMMDGDEQVE
YPLKPIVENAKPTLRQIMAHFSDVAEAYIEMRNKKEPYMPRYGLVRNLRDGSLARYAFDFYEVTSRTPVRA
REAHIQMKAAALKSAQSRLFGLDGGISTQEENTERHTTEDVSPSMHTLLGVKNM

Fig. 2

```
GGAAATGACACAATCGATGCAGGAGGAAGCACTAAGAAAGATGTAAAACAAGAGCAAGGTAGCATTCAACCA
AATCTCAACAAGGAAAAGGAAAAGGACTTGAATGTTGGAACATCTGGAACTCACACTGTGCCACGAATTAAA
GCTATCACGTCCAAAATGAGAATGCCCAAGAGTAAGGGTGCAACTGTACTAAATTTGGAACACTTACTCGAG
TATGCTCCACAGCAAATTGACATCTCAAATACTCGAGCAACTCAATCACAGTTTGATACATGGTATGAAGCA
GTACAACTTGCATACAACATAGGAGAAACTGAAATGCCAACTGTGATGAATGGGCTTATGGTTTGGTGCATT
GAAAATGGAACCTCGCCAAATATCAATGGAGTTTGGGTTATGATGGATGGAGATGAACAAGTCGAATACCCA
CTGAAACCAATCGTTGAGAATGCAAAACCAACACTTAGGCAAATCATGGCACATTTCTCAGATGTTGCAGAA
GCGTATATAGAAATGCGCAACAAGAAGGAACCATATATGCCACGATATGGTTTAGTTCGTAATCTGCGCGAT
GGAAGTTTGGCTCGCTATGCTTTTGACTTTTATGAAGTTACATCACGGACACCAGTGAGGGCTAGAGAGGCA
CACATTCAAATGAAGGCCGCAGCTTTAAAATCAGCTCAATCTCGACTTTTCGGATTGGATGGTGGCATTAGT
ACACAAGAGGAAAACACAGAGAGGCACACCACCGAGGATGTTTCTCCAAGTATGCATACTCTACTTGGAGTG
AAGAACATG
```

Fig. 3

XbaI           leader sequence of RNA4 of CMV

TCTAGA GTTATTGTCTACTGACTATATAGAGAGTGTGTGTGTGCTGTGTTTTCTCTTTTGTGTC
GTAGAATTGAGTCGAGTCATG

CP gene of PVY − T

GGAAATGACA CAATCGATGC AGGAGGAAGC ACTAAGAAAG ATGTAAAACA AGAGCAAGGT
AGCATTCAAC CAAATCTCAA CAAGGAAAAG GAAAAGGACT TGAATGTTGG AACATCTGGA
ACTCACACTG TGCCACGAAT TAAAGCTATC ACGTCCAAAA TGAGAATGCC AAGAGTAAG
GGTGCAACTG TACTAAATTT GGAACACTTA CTCGAGTATG CTCCACAGCA AATTGACATC
TCAAATACTC GAGCAACTCA ATCACAGTTT GATACATGGT ATGAAGCAGT ACAACTTGCA
TACAACATAG GAGAAACTGA AATGCCAACT GTGATGAATG GCTTATGGT TTGGTGCATT
GAAAATGGAA CCTCGCCAAA TATCAATGGA GTTTGGGTTA TGATGGATGG AGATGAACAA
GTCGAATACC CACTGAAACC AATCGTTGAG AATGCAAAAC CAACACTTAG GCAAATCATG
GCACATTTCT CAGATGTTGC AGAAGCGTAT ATAGAAATGC GCAACAAGAA GGAACCATAT
ATGCCACGAT ATGGTTTAGT TCGTAATCTG CGCGATGGAA GTTTGGCTCG CTATGCTTTT
GACTTTTATG AAGTTACATC ACGGACACCA GTGAGGGCTA GAGAGGCACA CATTCAAATG
AAGGCCGCAG CTTTAAAATC AGCTCAATCT CGACTTTTCG GATTGGATGG TGGCATTAGT
ACACAAGAGG AAAACACAGA GAGGCACACC ACCGAGGATG TTTCTCCAAG TATGCATACT
CTACTTGGAG TGAAGAACAT G    TGAGAGCTC
                        Sst I
               termination
                 codon

Fig. 4

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 801 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Potato Virus Y-T (xi) SEQUENCE DESCRIPTION: SEQ ID NO:1:

```
GGAAATGACA CAATCGATGC AGGAGGAAGC ACTAAGAAAG ATGTAAAACA AGAGCAAGGT      60

AGCATTCAAC CAAATCTCAA CAAGGAAAAG GAAAAGGACT TGAATGTTGG AACATCTGGA     120

ACTCACACTG TGCCACGAAT TAAAGCTATC ACGTCCAAAA TGAGAATGCC CAAGAGTAAG     180

GGTGCAACTG TACTAAATTT GGAACACTTA CTCGAGTATG CTCCACAGCA AATTGACATC     240

TCAAATACTC GAGCAACTCA ATCACAGTTT GATACATGGT ATGAAGCAGT ACAACTTGCA     300

TACAACATAG GAGAAACTGA AATGCCAACT GTGATGAATG GGCTTATGGT TTGGTGCATT     360

GAAAATGGAA CCTCGCCAAA TATCAATGGA GTTTGGGTTA TGATGGATGG AGATGAACAA     420

GTCGAATACC CACTGAAACC AATCGTTGAG AATGCAAAAC CAACACTTAG GCAAATCATG     480

GCACATTTCT CAGATGTTGC AGAAGCGTAT ATAGAAATGC GCAACAAGAA GGAACCTATA     540

ATGCCACGAT ATGGTTTAGT TCGTAATCTG CGCGATGGAA GTTTGGCTCG CTATGCTTTT     600

GACTTTTATG AAGTTACATC ACGGACACCA GTGAGGGCTA GAGAGGCACA CATTCAAATG     660

AAGGCCGCAG CTTTAAAATC AGCTCAATCT CGACTTTTCG GATTGGATGG TGGCATTAGT     720

ACACAAGAGG AAAACACAGA GAGGCACACC ACCGAGGATG TTTCTCCAAG TATGCATACT     780

CTACTTGGAG TGAAGAACAT G                                              801
```

(2) INFORMATION FOR SEQ ID NO:2:

(i) SEQUENCE CHARACTERISTICS:
        (A) LENGTH: 267 amino acids
        (B) TYPE: amino acid (C) STRANDEDNESS: single
        (D) TOPOLOGY: linear (ii) MOLECULE TYPE: PVY-T coat protein (iii) HYPOTHETICAL: NO (iv) ANTI-SENSE: NO (vi) ORIGINAL SOURCE:
        (A) ORGANISM: Potato Virus Y-T (xi) SEQUENCE DESCRIPTION: SEQ ID NO:2:

```
Gly Asn Asp Thr Ile Asp Ala Gly Gly Ser Thr Lys Lys Asp Val Lys
1               5                   10                  15

Gln Glu Gln Gly Ser Ile Gln Pro Asn Leu Asn Lys Glu Lys Glu Lys
            20                  25                  30

Asp Leu Asn Val Gly Thr Ser Gly Thr His Thr Val Pro Arg Ile Lys
        35                  40                  45

Ala Ile Thr Ser Lys Met Arg Met Pro Lys Ser Lys Gly Ala Thr Val
    50                  55                  60

Leu Asn Leu Glu His Leu Leu Glu Tyr Ala Pro Gln Gln Ile Asp Ile
65                  70                  75                  80

Ser Asn Thr Arg Ala Thr Gln Ser Gln Phe Asp Thr Trp Tyr Glu Ala
                85                  90                  95

Val Gln Leu Ala Tyr Asn Ile Gly Glu Thr Glu Met Pro Thr Val Met
            100                 105                 110

Asn Gly Leu Met Val Trp Cys Ile Glu Asn Gly Thr Ser Pro Asn Ile
        115                 120                 125

Asn Gly Val Trp Val Met Met Asp Gly Asp Glu Gln Val Glu Tyr Pro
    130                 135                 140

Leu Lys Pro Ile Val Glu Asn Ala Lys Pro Thr Leu Arg Gln Ile Met
145                 150                 155                 160

Ala His Phe Ser Asp Val Ala Glu Ala Tyr Ile Glu Met Arg Asn Lys
                165                 170                 175

Lys Glu Pro Tyr Met Pro Arg Tyr Gly Leu Val Arg Asn Leu Arg Asp
            180                 185                 190

Gly Ser Leu Ala Arg Tyr Ala Phe Asp Phe Tyr Glu Val Thr Ser Arg
        195                 200                 205

Thr Pro Val Arg Ala Arg Glu Ala His Ile Gln Met Lys Ala Ala Ala
    210                 215                 220

Leu Lys Ser Ala Gln Ser Arg Leu Phe Gly Leu Asp Gly Gly Ile Ser
225                 230                 235                 240

Thr Gln Glu Glu Asn Thr Glu Arg His Thr Thr Glu Asp Val Ser Pro
                245                 250                 255

Ser Met His Thr Leu Leu Gly Val Lys Asn Met
            260                 265
```

(2) INFORMATION FOR SEQ ID NO:3:

(i) SEQUENCE CHARACTERISTICS:
(A) LENGTH: 895 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
TCTAGAGTTA TTGTCTACTG ACTATATAGA GAGTGTGTGT GTGCTGTGTT TTCTCTTTTG      60
TGTCGTAGAA TTGAGTCGAG TCATGGGAAA TGACACAATC GATGCAGGAG GAAGCACTAA     120
GAAAGATGTA AACAAGAGC AAGGTAGCAT TCAACCAAAT CTCAACAAGG AAAAGGAAAA      180
GGACTTGAAT GTTGGAACAT CTGGAACTCA CACTGTGCCA CGAATTAAAG CTATCACGTC     240
CAAAATGAGA ATGCCCAAGA GTAAGGGTGC AACTGTACTA AATTTGGAAC ACTTACTCGA     300
GTATGCTCCA CAGCAAATTG ACATCTCAAA TACTCGAGCA ACTCAATCAC AGTTTGATAC     360
ATGGTATGAA GCAGTACAAC TTGCATACAA CATAGGAGAA ACTGAAATGC CAACTGTGAT     420
GAATGGGCTT ATGGTTTGGT GCATTGAAAA TGGAACCTCG CCAAATATCA ATGGAGTTTG     480
GGTTATGATG GATGGAGATG AACAAGTCGA ATACCCACTG AAACCAATCG TTGAGAATGC     540
AAAACCAACA CTTAGGCAAA TCATGGCACA TTTCTCAGAT GTTGCAGAAG CGTATATAGA     600
AATGCGCAAC AAGAAGGAAC CATATATGCC ACGATATGGT TTAGTTCGTA ATCTGCGCGA     660
TGGAAGTTTG GCTCGCTATG CTTTTGACTT TTATGAAGTT ACATCACGGA CACCAGTGAG     720
GGCTAGAGAG GCACACATTC AAATGAAGGC CGCAGCTTTA AAATCAGCTC AATCTCGACT     780
TTTCGGATTG GATGGTGGCA TTAGTACACA AGAGGAAAAC ACAGAGAGGC ACACCACCGA     840
GGATGTTTCT CCAAGTATGC ATACTCTACT TGGAGTGAAG AACATGTGAG AGCTC          895
```

(2) INFORMATION FOR SEQ ID NO:4:

(i) SEQUENCE CHARACTERISTICS:
        (A) LENGTH: 85 base pairs
        (B) TYPE: nucleic acid
        (C) STRANDEDNESS: double
        (D) TOPOLOGY: linear (ii) MOLECULE TYPE: DNA (genomic); leader sequence (iii) HYPOTHETICAL: NO (iv) ANTI-SENSE: NO (vi) ORIGINAL SOURCE:
        (A) ORGANISM: Cucumber mosaic virus (xi) SEQUENCE DESCRIPTION: SEQ ID NO:4:

```
TCTAGAGTTA TTGTCTACTG ACTATATAGA GAGTGTGTGT GTGCTGTGTT TTCTCTTTTG      60
TGTCGTAGAA TTGAGTCGAG TCATG                                           85
```

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Synthetic primer 1

(xi) SEQUENCE DESCRIPTION: SEQ ID NO:5:

```
AAAATCTAGA TGAAATGACA CAATCGATGC AGGAGGA                               37
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single -continued

```
        (D) TOPOLOGY: linear (ii) MOLECULE TYPE: Synthetic primer 2

(xi) SEQUENCE DESCRIPTION: SEQ ID NO:6:

TTTTGAGCTC TCACATGTTC TTCACTCCAA GTAGAG                                  36

(2) INFORMATION FOR SEQ ID NO:7:

(i) SEQUENCE CHARACTERISTICS:
          (A) LENGTH: 85 base pairs
          (B) TYPE: nucleic acid
          (C) STRANDEDNESS: single
          (D) TOPOLOGY: linear (ii) MOLECULE TYPE: Synthetic primer 3

(xi) SEQUENCE DESCRIPTION: SEQ ID NO:7:

GGGGATCCAC TAGTTCTAGA GTTTTCTCTT TTGTGTCGTA GAATTGAGTC GAGTCATGGG        60

AAATGACACA ATCGATGCAG GAGGA                                              85

(2) INFORMATION FOR SEQ ID NO:8:

(i) SEQUENCE CHARACTERISTICS:
          (A) LENGTH: 78 base pairs
          (B) TYPE: nucleic acid
          (C) STRANDEDNESS: single
          (D) TOPOLOGY: linear (ii) MOLECULE TYPE: Synthetic primer 4

(iii) HYPOTHETICAL: NO (iv) ANTI-SENSE: NO (xi) SEQUENCE DESCRIPTION: SEQ ID NO:8:

GGGATCCACT AGTTCTAGAG TTATTGTCTA CTGACTATAT AGAGAGTGTG TGTGTGCTGT        60

GTTTTCTCTT TTGTGTGT                                                      78
```

RECOMBINANT VECTOR, METHOD FOR GIVING IMMUNITY AGAINST PVY-T TO POTATO PLANT, AND POTATO PLANT HAVING IMMUNITY AGAINST PVY-T

The application is a continuation of application Ser. No. 08/139,157 filed on Oct. 21, 1993, now abandoned.

BACKGROUND OF THE INVENTION

I. Field of the Invention

This invention relates to a recombinant vector which can confer upon potato plants immunity against potato virus Y necrosis line (hereinafter also referred to as "PVY-T"). This invention also relates to a method for conferring immunity against PVY-T upon potato plants and to a potato plant having immunity against PVY-T.

II. Description of Related Art

PVY-T causes tobacco yellow spot necrosis which causes severe necrosis in tobacco. PVY-T is transferred by aphids. If potato plants infected with PVY-T are cultivated, PVY-T may be transferred by aphids, thereby causing severe damage to tobacco. Although PVY-T may cause mosaic disease in potato plants, the symptoms are slight and unclear in a number of varieties, so that it is difficult to remove the diseased plants during cultivation of seed potatoes. Therefore, the diseased potato plants may serve as a source of PVY-T.

With some potato varieties, inoculation of PVY-T causes necrosis spots in the inoculated leaf in the present generation, while in the next generation, symptoms are not observed and infection by PVY-T can not be detected. If these potato varieties are bred by cross breeding, PVY-T-resistant potato plants may be obtained. However, it is expected that it takes as long as 10 years or more to obtain a variety resistant to PVY-T by this method. If resistance to PVY-T can be conferred upon potato plants by genetic engineering techniques, PVY-T-resistant potato plants can be obtained in a short period of time, which is very advantageous.

A method for conferring upon a plant resistance against a virus is known, in which the gene encoding the coat protein (hereinafter also referred to as "CP") of the virus is introduced to the plant (Japanese Laid-open Patent Application (Kokai) Nos. 62-201527 and 62-285791; Plant Cell Technology Vol. 4, No. 2 (1992) pp.101–109, Bio/Technology 8, 127–134 (1990)). According to this method, although resistance against the virus is conferred upon the plant, the plant produces the CP of the virus. If a plant produces a virus CP, amino acids and energy are consumed for the production of virus CP, so that the growth of the plant is not as good as other plants which do not produce the virus CP. Further, in a plant such as potato which is used as a food, the safety of the CP with respect to health must be investigated. Thus, if a plant which is resistant to a virus does not produce the virus CP is obtained, it is very advantageous.

SUMMARY OF THE INVENTION

Accordingly, an object of the present invention is to provide a recombinant vector by which immunity against PVY-T may be conferred upon potato plants without making the plants produce the CP of PVY-T. Another object of the present invention is to provide a method for conferring upon potato plants immunity against PVY-T. Still another object of the present invention is to provide a potato plant having immunity against PVY-T.

The present inventors intensively studied to find that immunity against PVY-T may be conferring upon potato plants without making the potato plants produce the CP of PVY-T by transforming the potato plants with a recombinant vector containing a gene encoding the CP of PVY-T (SEQ ID NO:1) at a downstream region of the leader sequence of RNA4 (SEQ ID NO:4) of cucumber mosaic virus (hereinafter also referred to as "CMV"), thereby completing the present invention.

That is, the present invention provides a recombinant vector comprising a promoter which functions in a potato plant cell; an operably linked leader sequence of RNA4 of CMV (SEQ ID NO:4), which is located downstream of said promoter; and an operably linked sequence which encodes a CP of PVY-T, (SEQ ID NO:1) which is located downstream of said leader sequence; said recombinant vector being capable of transforming potato plants. The present invention also provides a method for conferring immunity against PVY-T upon a potato plant, comprising transforming said potato plant with said recombinant vector according to the present invention. The present invention still further provides a potato plant having immunity against PVY-T, which was prepared by the method according to the present invention.

By the present invention, a potato plant having immunity against PVY-T, which does not produce CP of PVY-T, was first provided. Therefore, the present invention is effective for the prevention of tobacco yellow spot necrosis and other diseases of potato plants in which PVY-T participates.

BRIEF DESCRIPTION OF THE DRAWINGS

FIG. 2 shows the amino acid sequence (SEQ ID NO:2) of the CP of the PVY-T which was used in the examples of the present invention;

FIG. 3 shows the nucleotide sequence of the CP gene (SEQ ID NO:1) of the PVY-T which was used in the examples of the present invention; and FIG. 4 shows the determined nucleotide sequence (SEQ ID NO:3) of the DNA fragment inserted in pBIPT(CML) which was prepared in the examples of the present invention.

DETAILED DESCRIPTION OF THE PREFERRED EMBODIMENTS

Figure 1:
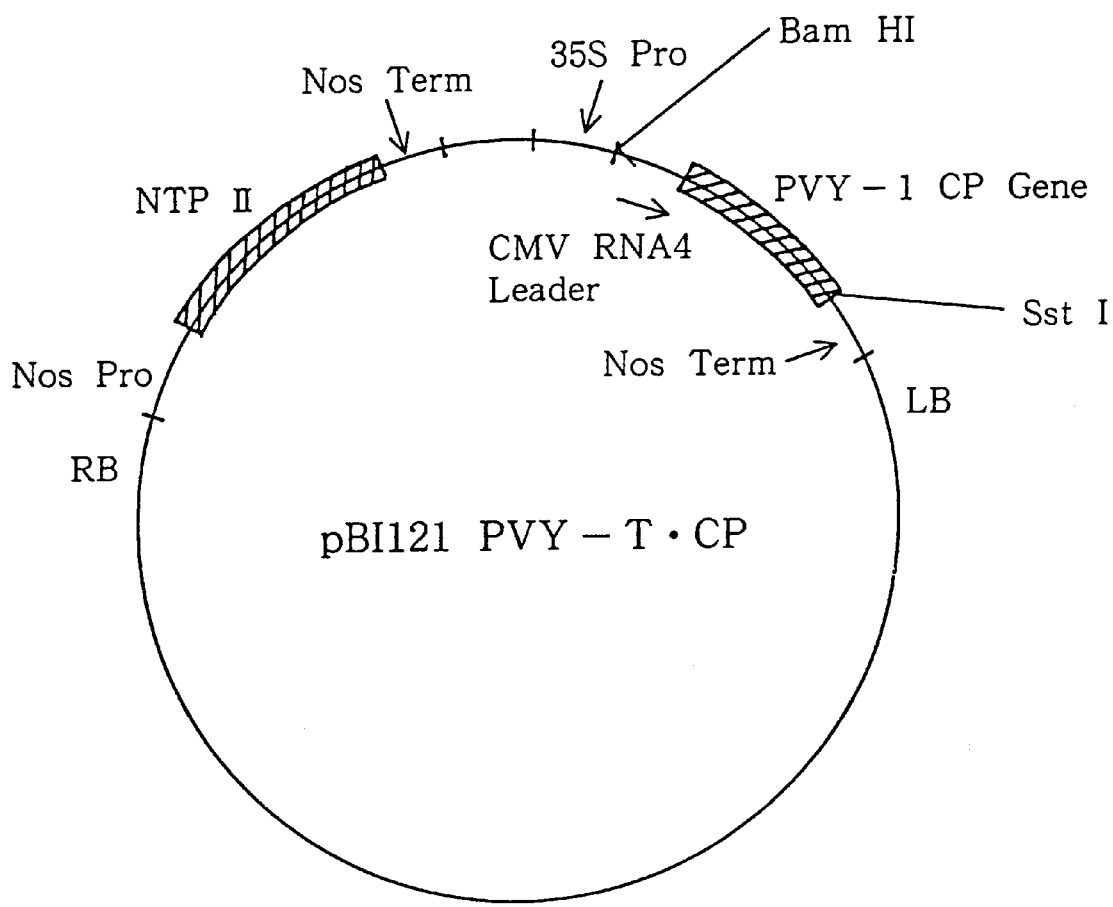
FIG. 1 is a gene map showing pBIPT(CML) which is an example of the recombinant vector according to the present invention.

In the present invention, the term "immunity against PVY-T" means that after inoculation of PVY-T to a potato plant, the potato plant is not diseased and the potato plant is not made to be a carrier of PVY-T. In other words, the proliferation of PVY-T in the potato plant is not detected.

The leader sequence of RNA4 of CMV which is inserted in the recombinant vector according to the present invention is known and described in Nitta et al., Japan Plant Pathology Association Journal, Vol. 54, pp.516–522. The nucleotide sequence of the leader sequence of RNA4 of CMV, which was used in the examples described below is as follows, which is also shown in Sequence ID No. 4 (1st to 85th nucleotide):

TCTAGAGTTATTGTCTACTGACTATATAGAGAGTGT
   GTGTGTGCTGTGTTTTCTCTTTTGTGTCGTAG
   AATTGAGTCGAGTCATG

The leader sequence of RNA4 of CMV can easily be prepared by chemical synthesis, by excising it from the CMV genome, or by amplifying the sequence by the PCR method using the CMV genome as a template.

Downstream the above-described leader sequence of RNA4 of CMV, a gene encoding the CP of PVY-T is operably inserted. The amino acid sequence of the CP of PVY-T as well as the nucleotide sequence encoding the same is known. The amino acid sequence and the nucleotide sequence used in the examples below are shown in FIGS. 2 and 3, as well as in Sequence ID Nos. 2 and 1. The gene encoding the CP of PVY-T can easily be prepared by a conventional method such as the PCR method using the PVY-T genome as a template.

The above-described leader sequence of RNA4 of CMV and the gene encoding the CP of PVY-T are inserted downstream of a promoter in an operable manner. The promoter may be any known promoter which can carry out transcription in potato plant cells. Examples of such a promoter include the 35S promoter of cauliflower mosaic virus, NOS promoter of Agrobacterium, Class-I patatin promoters of potato, and rbcS promoters of plants, although the promoter which can be used is not restricted thereto. Among these, the 35S promoter of cauliflower mosaic virus is preferred.

The recombinant vector according to the present invention may be based on any vector which can transform potato plants and which can replicate in potato plant cells. The vector has a replication origin which functions in potato plant cells and may preferably have a terminator and an appropriate selection marker such as a drug resistance maker. Such a vector is well-known and is commercially available. In the examples below, pBI121 which is a plasmid vector functioning in plant cells, which is commercially available from CLONETECH, USA, is used. The gene map of an example of the recombinant vector according to the present invention, which was prepared in the examples below, in which the above-described leader sequence of RNA4 and the CP gene of PVY-T are inserted, is shown in FIG. 1.

It is well-known in the art that even if a small number of nucleotides in a DNA are substituted, deleted or inserted, the function of the DNA may not be substantially affected. Therefore, even if the nucleotide sequence of a leader sequence of RNA4 of CMV and/or the amino acid sequence encoded by or the nucleotide sequence of CP gene of PVY-T are different from those described in FIGS. 2 and 3, respectively, because of slight substitution, deletion or insertion, as long as the recombinant vector can transform potato plants so as to give to the potato plant immunity against PVY-T without making the potato plant produce CP of PVY-T, the leader sequence of RNA4 and the gene encoding CP of PVY-T are construed as within the scope of the terminologies of "leader sequence of RNA4 of cucumber mosaic virus" and "sequence which encodes a coat protein of potato virus Y necrosis line" in the present claims. For example, as for the CP of PVY-T, while the CP of the PVY-T isolated in the Netherlands (Van Der Vlugt et al., (1989) J. Gen. Virology 70, 229–233) or of the PVY-T published by the group of Hokkaido University (OSHIMA et al., (1991), Japan Plant Pathology Association Journal, 57, 615–622) have amino acid sequences different from that shown in FIG. 2 or Sequence ID No. 2 which was used in the examples below in 2 or 3 amino acids, the sequences encoding these amino acid sequences are also within the scope of the terminology "sequence which encodes a coat protein of potato virus Y necrosis line" in the claims. Further, needless to say, since nucleotide sequences encoding amino acid sequences have degeneracy, the sequences which encode the amino acid sequence shown in FIG. 2 or Sequence ID No. 2, but have different nucleotide sequences from that shown in FIG. 3 or Sequence ID No. 1, are included in the terminology "sequence which encodes a coat protein of potato virus Y necrosis line" in the claims.

The recombinant vector according to the present invention can easily be prepared by inserting the above-mentioned leader sequence of RNA4 of CMV and the sequence encoding CP of PVY-T into the above-mentioned vector by a well-known conventional method employing restriction enzymes. A specific example for constructing the recombinant vector according to the present invention is described in detail in the examples hereinbelow described.

Potato plants may be transformed with the recombinant vector according to the present invention, preferably, by a method in which *Agrobacterium tumefaciens* which a strongly infects plants is first transformed and the transformed *Agrobacterium tumefaciens* is then inoculated to a potato plant, although the method of transformation is not restricted to this method. The above-mentioned transformation method utilizing *Agrobacterium tumefaciens* is known in the art, and can be carried out by the freeze-thaw method (G. An et al., (1988) Binary Vectors, In Plant Molecular Biology Manual A3, Kluwer Academic, Dordrecht pp.1–19).

As will be concretely shown in the examples hereinbelow described, by transforming potato plants with the recombinant vector according to the present invention, immunity against PVY-T can be conferred upon potato plants. Moreover, in the potato plants to which immunity against PVY-T was conferred by the method of the present invention, although the CP gene of PVY-T is transcribed, CP is not produced. Further, the potatoes prepared by the method of the present invention have the same morphologies as those of normal potatoes.

The present invention will now be described by way of examples thereof. It should be noted that the examples are presented for illustration purposes only and should not be interpreted in any restrictive way.

EXAMPLE (1) Isolation of CP Gene of PVY-T

A lyophilized sample of a tobacco leaf infected by PVY-T (UDAGAWA et al., 1972, Japan Plant Association Journal 38, 210) was inoculated to leaves of tobacco plants to obtain systemically infected tobacco plants. From the ground leaves, PVY-T was purified by fractionating centrifugation. To the obtained purified PVY-T, sodium dodecyl sulfate was added to a final concentration of 1 wt % to dissociate RNA from the CP. From the resultant, RNA was separated by sucrose density gradient centrifugation (0–32.5 wt % sucrose, 39,000 rpm, 4 hours). To the separated RNA, ethanol was added to a final concentration of 70 wt % to precipitate the RNA and the precipitated RNA of PVY-T was recovered by centrifugation. To the thus obtained RNA, primer 1 (SEQ ID NO:5) (see Table 1) was added and cDNA was prepared using M-MLV reverse transcriptase (commercially available from BRL, USA) in accordance with the instructions attached to the commercial product. To the obtained cDNA, primer 1 and primer 2 (SEQ ID NO:6) (see Table 1) were added and the resultant was subjected to polymerase chain reaction (PCR) after adding Taq DNA polymerase (commercially available from TAKARA SHUZO CO., LTD, Kyoto, JAPAN). The PCR was carried out in the buffer described in the instructions at 93° C., 1 minute, 42° C., 1 minute and 72° C., 1 minute, and this thermal cycle was repeated 30 times, thereby amplifying the CP gene. Both ends of the amplified DNA were cut off using Sst I and Xba I, and the digest was subjected to electrophoresis on 1.2 wt % agarose. The desired DNA was then recovered using DEAE cellulose membrane NA45 (commercially available from Schleicher & Schuell, USA).

FIG. 4 and Sequence ID NO: 3. As shown, it was confirmed that a plasmid pPTCP(CML) having the leader sequence of RNA4 of CMV upstream of the CP gene of PVY-T was obtained.

TABLE 1

| | Nucleotide Sequence of Primers Used |
|---|---|
| Primer 1: | 5'AAAATCTAGATGAAATGACACAATCGATGCAGGAGGA3' |
| Primer 2: | 5'TTTTGAGCTCTCACATGTTCTTCACTCCAAGTAGAG3' |
| Primer 3: | 5'GGGGATCCACTAGTTCTAGAGTTTTCTCTTTTGTGTCGTAGAATT GAGTCGAGTCATGGGAAATGACACAATCGATGCAGGAGGA3' |
| Primer 4: | 5'GGGATCCACTAGTTCTAGAGTTATTGTCTACTGACTATATAGAGA GTGTGTGTGTGCTGTGTTTTCTCTTTTGTGTGT3' |

The recovered DNA was inserted into plasmid pBluescript II SK(+) (commercially available from STRATAGENE, USA) which had been digested with restriction enzymes Sst I and Xba I. *E. coli* JM109 was transformed with the resulting plasmid (pPTCP). From the obtained colonies, plasmid pPTCP was recovered and digested with restriction enzymes Sst I and Xba I. As a result, insertion of the CP gene of PVY-T, having a size of about 0.8 kb, was confirmed.

(2) Determination of the Nucleotide Sequence of the CP Gene of PVY-T

Plasmid pPTCP was denatured using 0.4 M NaOH (37° C., 5 minutes) and precipitated by ethanol, followed by evaporation to dryness. Using the thus obtained sample, the nucleotide sequence of the CP gene of PVY-T was determined using a T7 DNA polymerase sequencing kit (commercially available from PHARMACIA) and primers (M4 and RV, commercially available from TAKARA SHUZO CO., LTD).

(3) Insertion of RNA4 Leader Sequence of CMV

*E. coli* BW313 (Kunkel, T. A. (1985) Proc. Natl. Acad. Sci. USA., 82, 488–492, commercially available from TAKARA SHUZO CO., LTD.) transformed with plasmid pPTCP was cultured in liquid medium. When the absorbance at 600 nm reached 0.4, helper phage M13K07 was added and the resultant was cultured overnight in the presence of kanamycin (70 μg/ml). The culture medium was centrifuged at 15,000 rpm for 15 minutes and polyethylene glycol 6000 and NaCl were added to the supernatant to a final concentrations of 4 wt % and 0.5 M, respectively. After leaving the resultant to stand in ice for 1 hour, phage was precipitated by centrifugation at 15,000 rpm for 15 minutes. The recovered phage was suspended in TE (10 mM Tris-HCl, 1 mM EDTA, pH 8.0), and an equivolume of water-saturated phenol/chloroform (1:1) was added, followed by stirring for 5 minutes. The resultant was centrifuged at 15,000 rpm for 15 minutes and the obtained supernatant was subjected to ethanol precipitation to obtain a template DNA. To the thus obtained template DNA, primer 3 (SEQ ID NO:7) (see Table 1) was added and a part of the leader sequence of RNA4 of CMV was inserted using a site-specific recombination kit MUTAN-K (commercially available from TAKARA SHUZO CO., LTD.) to obtain plasmid pPTCP(CM). The thus obtained plasmid pPTCP(CM) was then used as a template so as to introduce the remaining leader sequence by using primer 4 (SEQ ID NO:8) (see Table 1). The nucleotide sequence of the insert in the plasmid was determined in the same manner as described above. The determined nucleotide sequence is shown in (4) Construction of Recombinant Vector for Transforming Plants From plant expression vector pBI121 (commercially available from CLONETECH, USA), the β-glucronidase gene was removed by restriction enzymes Xba I and Sst I, and the resulting vector fragment was recovered by electrophoresis on 0.8 wt % agarose gel. The thus recovered fragment originated from pBI121 and plasmid pPTCP (CML) sufficiently digested with Xba I and Sst I were ligated, and *E. coli* JM109 was transformed with the ligation product. The resultant was cultured on LB plates containing 30 μg/ml of kanamycin, and a recombinant vector pBIPT (CML) shown in FIG. 1 for transforming plants was obtained from the formed colonies.

(5) Transformation of *Agrobacterium tumefaciens*

By the freeze-thaw method, *Agrobacterium tumefaciens* LBA4404 (Hockman et al., Nature 303:179–183, 1983) was transformed with the vector pBIPT (CML) expressing the CP of PVY-T to obtain *Agrobacterium tumefaciens* LBA4404 (pBIPT(CML)).

(6) Transformation of Potato Plants

Potato plants were transformed by using *Agrobacterium tumefaciens* LBA4404 (pBIPT(CML)) obtained in (5). Potato varieties May Queen, Toyoshiro, Danshaku (varieties of Japan) and Saco (variety of USA) were subjected to the transformation. Virus-free plants of these varieties were aseptically grown in a medium containing inorganic salts of Linsmaier and Skoog (1965), 30 g/l of sucrose, and agar (0.8 wt %). The leaves of the thus grown virus-free plants were cut into pieces of 0.6–1.0 cm×0.5–1.0 cm, and the stems (which may or may not contain nodes) were cut into pieces having a length of 0.5–2.0 cm. These pieces of the leaves and stems were cultured together with about $10^8$ cells of *Agrobacterium tumefaciens* LBA4404 (pBIPT(CML)) in a liquid medium containing inorganic salts of Linsmaier and Skoog and 30 g/l of glucose at 25° C. for 48 hours. The pieces of leaves and stems were washed 2–3 times with sterilized water containing 250 mg/l of cefotaxim to wash off bacteria and the pieces were then placed on the regeneration media having compositions shown in Tables 2 and 3. In case of using the regeneration medium (LSZK100) shown in Table 3, kanamycin-resistant calli emerged from the implanted pieces of leaves and stems about 20 days after beginning of the culture. These calli were cultured on the above-mentioned medium for another 10–30 days, and kanamycin-resistant leaves and stems regenerated. The regenerated leaves and stems were cut into pieces and the pieces were cultured on an agar (0.8 wt %) medium containing inorganic salts of Linsmaier and Skoog, 30 g/l of sucrose, 250 mg/l of cefotaxim and 100 mg/l of kanamycin.

In cases where the regeneration medium (KS1) shown in Table 2 was used, the formation of calli and regeneration of plants were slower than in cases where LSZK100 was used. The number of transformants obtained by the above-described method is shown in Table 4.

TABLE 2

Composition of Regeneration Medium (KS1 Medium)

| Component | Concentration (mg/l) |
| --- | --- |
| MS Medium* from Which NH$_4$NO$_3$ is Removed | |
| NH$_4$NO$_3$ | 300.0 |
| Indole Acetic Acid (IAA) | 0.3 |
| Zeatin | 2.0 |
| Coconut Water** | 2.0(wt%) |
| Sucrose | 3,000.0 |
| Mannitol | 35,000.0 |
| Kanamycin | 100.0 |
| Cefotaxim | 250.0 |
| Gellan Gum (Gelrite) | 2,000.0 |
| (pH 5.8) | |

*: Murashige and Skoog's medium (1962)
**: commercially available from GIBCO

TABLE 3

Composition of Regeneration Medium (LSZK100 Medium)

| Component | Concentration (mg/l) |
| --- | --- |
| LS Basal Medium | |
| myo-Inositol | 100.0 |
| Thiamine HCl | 1.0 |
| Indole Acetic Acid (IAA) | 0.1 |
| Zeatin Riboside | 1.0 |
| Sucrose | 20,000.0 |
| Kanamycin | 100.0 |
| Cefotaxim | 250.0 |
| Agar | 8,000.0 |
| (pH 5.8) | |

TABLE 4

| Variety | Number of Regenerated Plants |
| --- | --- |
| May Queen (variety of Japan) | 64 |
| Toyoshiro (variety of Japan) | 28 |
| Danshaku (variety of Japan) | 6 |
| Saco (variety of USA) | 53 |

(7) Test for Resistance to PVY-T of Transformants

To the thus obtained transformants of varieties May Queen, Toyoshiro, Danshaku and Saco, PVY-T was inoculated. After the inoculation, the amounts of the virus carried by the transformants were tested by ELISA and by using tobacco BY4 strain as an indicator. More particularly, purified virus particles of PVY-T were inoculated to tobacco BY4 which is an indicator of PVY-T. Two weeks later, after confirming the necrosis of the plants, infected leaves were sampled and homogenized in PBS-T buffer (phosphate buffer, 0.02 M) having a weight of 2–10 times that of the raw weight of the leaves. The obtained homogenized fluid was inoculated to each transformant. The transformants were cultivated in an incubator illuminated for 16 hours a day at 23° C. in daytime and at 17° C. at night after the transformants had been transferred to cultivation pots. The inoculation was carried out 2–3 weeks after the transfer to the cultivation pots. The uppermost leaf to the 5th leaf from the upper end of each plant were subjected to the inoculation. The inoculation was carried out by applying a mixture of the above-mentioned homogenized fluid and 600 mesh carborundum (10 wt %). After the inoculation, leaves were sampled at several time points (1 week to 2 months) and the virus in the homogenized fluid of each sample was quantified by ELISA. The ELISA was carried out in a conventional manner. That is, anti-PVY-T polyclonal antibody as a primary antibody was immobilized in the wells of a microtiter plate. After blocking of the wells, each sample was placed in a well and reaction was allowed to occur. Then anti-PVY-T monoclonal antibody labelled with alkaline phosphatase as a secondary antibody was added to each well and reaction was allowed to occur. After washing the wells, disodium p-nitrophenyl phosphate as a substrate was added and the absorbance at 405 nm was measured. In the test using tobacco BY4 as an indicator, each homogenized fluid of each transformant of potato plants was diluted 10-fold or 100-fold and the diluted fluid was inoculated to tobacco BY4. After 2–3 weeks of the inoculation, the tobacco plants were examined for the outbreak of the disease. The results of the ELISA and the results of the test using the indicator were substantially commensurate. From the results, it was confirmed that transformants resistant to PVY-T and transformants having immunity against PVY-T were obtained. In Table 5, the term "transformant resistant to PVY-T" means a transformant in which proliferation of PVY-T was observed but the amount of the virus was smaller than those in the diseased plants. As mentioned above, the term "transformant having immunity against PVY-T" means that proliferation of the virus after the inoculation was not observed at all. Thus, by this test, it was confirmed that potato plants having immunity against PVY-T, which was not diseased and which did not carry the virus was obtained.

TABLE 5

Results of PVY-T Inoculation Test of Varieties

| Variety | Number of Plants Tested | Number of Plants Diseased | Number of Plants Resistant to PVY-T | Number of Plants Having Immunity against PVY-T |
| --- | --- | --- | --- | --- |
| May Queen | 51 | 41 | 2 | 8 |
| Danshaku | 3 | 3 | 0 | 0 |
| Saco | 16 | 10 | 1 | 5 |
| Toyoshiro | 3 | 1 | 0 | 2 |

To the transformants having immunity against PVY-T, as much as about 100 μg/ml of PVY-T was inoculated using the infected leaves of tobacco (BY4) as an inoculation source. However, PVY-T was not detected by the above-described ELISA (the detection limit of PVY-T by ELISA is about 10 ng). The immune transformants of May Queen, Toyoshiro and Saco were tested for the production of CP of PVY-T by ELISA. As a result, the CP of PVY-T was not detected in any of the tested transformants (the detection limit of CP of PVY-T by ELISA is about 10 ng). The diseased plants of May Queen were tested for the production of CP of PVY-T by ELISA. As a result, 5–10 μg of virus particles per 1 g of raw weight of the plants was detected.

To the transformants having immunity against PVY-T, PVY normal line, PVS and PVX were inoculated respectively. As a result, resistances to these viruses were not observed.

(8) Confirmation of Transcription of CP Gene by Northern Blotting Analysis

Transformants YA48 (May Queen), YA51 (May Queen) and YF1 (Toyoshiro), which have immunity against PVY-T, were tested for the transcription of the CP gene by Northern blotting analysis. That is, total RNAs were extracted from the leaves of each of these three transformants, and the RNAs were denatured by glyoxal and dimethylsulfoxide according to the method of Thomas (Thomas, Proc. Natl. Acad. Sci. USA 77:5201–5205 (1980)), followed by agarose gel electrophoresis to separate RNAs. The RNAs were transferred to a nylon membrane (GENE SCREEN PLUS™, commercially available from Du Pont) and Northern analysis was carried out using Xba I—Sac I fragment of plasmid pBIPT(CML) which had been labelled with $^{32}$P by random prime method using a commercially available kit (AMERSHAM®). The Northern blotting analysis revealed that an mRNA having a size of 1.0–1.4 kb was transcribed in each of YA48, YA51 and YF1. This size is coincident with the size of the mRNA which is transcribed from the CP gene. In the parent lines of May Queen and Toyoshiro which were tested as controls, transcription of such an mRNA was not detected. These results indicate that mRNA of the CP gene is transcribed in these three plants.

(9) Morphologies of Transformants

The immune transformants obtained in (7) as well as their parent lines (non-transformants) were cultivated in a closed incubator at 23° C. (day) and at 17° C. (night). As a result, the morphologies and growth characteristics of all the immune transformants were the same as those of the parent lines and the shape of tubers was the same of those of the parent lines.

---

We claim:

1. A recombinant vector, comprising:

a promoter which functions in potato plant cells;

a linked leader polynucleotide of RNA4 of cucumber mosaic virus, which is located downstream of said promoter; and a linked polynucleotide sequence which encodes a coat protein of potato virus Y necrosis line, which is located downstream of said leader polynucleotide, said recombinant vector being capable of transforming potato plants wherein potato plants containing cells transformed with said recombinant vector do not express said coat protein.

2. The recombinant vector according to claim 1, wherein said leader polynucleotide of RNA4 of cucumber mosaic virus has the nucleotide sequence from the 1st to 85th nucleotide of the sequence shown in SEQ ID NO: 4.

3. The recombinant vector according to claim 1, wherein said polynucleotide encoding said coat protein of potato virus Y necrosis line encodes the amino acid sequence shown in SEQ ID NO: 2.

4. The recombinant vector according to claim 3, wherein said polynucleotide encoding said coat protein of potato virus Y necrosis line comprises SEQ ID NO:1.

5. The recombinant vector according to claim 1, wherein said leader polynucleotide of RNA4 of cucumber mosaic virus and said polynucleotide which encodes a coat protein of potato virus Y necrosis line linked thereto comprises SEQ ID NO:3.

6. The recombinant vector according to claim 1, wherein said promoter which functions in potato plant cells is selected from the group consisting of the 35S promoter of cauliflower mosaic virus, the NOS promoter of Agrobacterium, Class-I patatin promoters of potato, and the rbcS promoters.

7. The recombinant vector according to claim 1, wherein said promoter is the 35S promoter of cauliflower mosaic virus.

8. A recombinant vector, comprising:

a promoter which functions in potato plant cells;

a linked leader polynucleotide of RNA4 of cucumber mosaic virus, which is located downstream of said promoter; and a linked polynucleotide sequence which encodes a coat protein of potato virus Y necrosis line, which is located downstream of said leader polynucleotide and which is located in the sense direction, said recombinant vector being capable of transforming potato plants wherein potato plants containing cells transformed with said recombinant vector do not express said coat protein.

* * * * *